United States Patent [19]
DeBold

[11] Patent Number: 6,117,644
[45] Date of Patent: Sep. 12, 2000

[54] PREDICTING AND DETECTING CARDIAC ALLOGRAFT REJECTION

[75] Inventor: Adolfo J. DeBold, Manotick, Canada

[73] Assignee: Ottawa Heart Institute Research Corporation, Ottawa, Canada

[21] Appl. No.: 09/090,313

[22] Filed: Jun. 4, 1998

[51] Int. Cl.[7] .................................................. G01N 33/53
[52] U.S. Cl. ........................ 435/7.1; 435/7.1; 435/7.21; 435/7.93; 435/7.94; 436/86; 436/518; 436/536; 436/811; 436/817
[58] Field of Search ..................................... 435/7.1, 7.21, 435/7.93, 7.94; 436/86, 518, 536, 811, 817

[56] References Cited

U.S. PATENT DOCUMENTS 5,786,163  7/1998  Hall ......................................... 435/7.92

FOREIGN PATENT DOCUMENTS

| 0 542 255 A1 | 5/1993 | European Pat. Off. . |
| 9324531 | 12/1993 | WIPO . |
| WO 97/32900 | 12/1997 | WIPO . |

OTHER PUBLICATIONS

White et al, Principles of Biochemistry, Third Edition, McGraw–Hill Book Company, 1964, pp. 706–708, 724.

Yokota et al, Dissociation of Cardiac Hypertrophy, Myosin Heavy Chain Isoform Expression, and Natriuretic Peptide Production in DOCA–Salt Rats, American Journal of Hypertension, Ltd. 1995; 8:301–310.

Hall et al, Prognostic Value of N–Terminal Proatrial Natriuretic Factor Plasma Levels Measured Wwithin the First 12 Hours after Myocardial Infarction, American College of Cardiology, vol. 26, No. 6, 1995; 1452–6.

Lerman, et al, Circulating N–Terminal Atrial Natriuretic Peptide as a Marker for Symptomless Left–Ventricular Dysfunction, The Lancet, May 1, 1993, vol. 341, 1105–9.

Motwani et al, Plasma Brain Natriuretic Peptide as an Indicator for Angiotensin–Converting–Enzyme Inhibition after Myocardial Infarction, The Lancet, May 1, 1993, vol. 341, 1109–13.

Davis et al, Atrial Natriuretic Peptide Levels in the Prediction of Congestive Heart Failure Risk in Frail Elderly, JAMA, May 20, 1992, vol. 267, No. 19, 2625–2629.

Takemura et al, Venticular Expression of Atrial and Brain Natriuretic Peptides in Patients with Myocarditis, International Journal of Cardiology, 52 (1995) 213–222.

Arad et al, Brain and Atrial Natriuretic Peptides in Patients with Ischemic Heart Disease with and without Heart Failure, General Cardiology, 1996; 87:12–17.

Masters, et al, Neuroendocrine Response to Cardiac Transplantation, Cardiovascular Medicine, vol. 9, No. 7, Sep., 1993, 609–617.

Kanda et al, Effect of Combination Therapy with OK432 and Recombinant Human Interferon–α A/D on Atrial Natriuretic Peptide Gene Expression in Mice with Viral Myocarditis, Journal of Pharcology and Experimental Therapeutics, vol. 274, No. 1, 494–498.

Hunt et al, The Amino–Terminal Portion of Pro–Brain Natriuretic Peptide (Pro–BNP) Circulates in Human Plasma, Biochemical and Biophysical Research Communications, Sep. 25, 1995, vol. 214, No. 3, pp. 1175–1183.

Geny, B. et al, Transient Reduction without Normalization of Brain Natriuretic Peptide Early after Heart Transplantation, The Journal of Thorac and Cardiovascular Surgery, 1998; 115:473–5.

Ationu, et al, Cardiac Transplantation Affects Ventricular Expression of Brain Natriuretic Peptide, Cardiovascular Research, 1993; 27:188–191.

Ationu, et al, Ventricular Expression of Brain Natriuretic Peptide Gene Following Orthotopic Cardiac Transplantation in Children—a Three Year Follow up, Cardiovascular Research 1993; 27:2135–2139.

*Primary Examiner*—David Saunders
*Attorney, Agent, or Firm*—Evenson, McKeown, Edwards & Lenahan, P.L.L.C.

[57] ABSTRACT

A method of diagnosing cardiac transplant rejection within a patient comprising, obtaining a sample of a biological fluid from the patient, and determining the level of a brain natriuretic peptide (BNP) or a fragment thereof, within the sample of body fluid. The step of determining the concentration of BNP involves an assay comprising at least one antibody exhibiting affinity for the BNP or a fragment thereof, and the biological fluid comprises plasma, urine or cerebrospinal fluid. Furthermore, the antibody used within the method may comprises a polyclonal antibody, a monoclonal antibody, or a combination thereof. Preferably, the method involves obtaining at least two of the samples of body fluid from the patient over a period of time and comparing the BNP levels, with an increase in BNP being indicative of an upcoming rejection episode.

27 Claims, 4 Drawing Sheets

PREDICTING AND DETECTING CARDIAC ALLOGRAFT REJECTION

The present invention relates to a method for the prediction and diagnosis of cardiac allograft rejection.

BACKGROUND OF THE INVENTION

The cardiac natriuretic peptides (NP) atrial natriuretic factor (ANF) and brain natriuretic peptide (BNP) are polypeptide hormones synthesized, stored and released by cardiac muscle cells (cardiocytes). In many ways, the endocrine heart is a modulator of systems such as the sympathetic nervous system, the renin-angiotensin-aldosterone system and other determinants of vascular tone, extracellular fluid volume and renal function.

ANF and BNP are synthesized by cardiocytes as prepro-hormones that are enzymatically processed to yield prohormones and, ultimately, hormones that are released into the circulation. In humans, the prohormone proANF is a polypeptide that contains 126 amino acids ($ANF_{1-26}$) that is processed to $ANF_{1-98}$ and $ANF_{99-126}$, the latter being the biologically active portion. Human proBNP, on the other hand, is 108 amino acids long and it is processed to $BNP_{1-76}$ and $BNP_{77-108}$, the latter being the biologically active peptide. Both the C-terminal and N-terminal portions of NPs circulate in blood. For example, Hunt et al (1995, Biochem Biophys Res Comm 214:1175–1183) report the detection of hBNP and N-terminal ProBNP within human plasma, and note an increase in the plasma levels of both peptides with congestive heart failure.

Under certain pathophysiological conditions affecting the cardiovascular system, synthesis and release of both ANF and BNP are significantly augmented in both atrial and ventricular cardiocytes. Increased production of ANF and BNP by the mammalian ventricle is a hallmark of cardiac hypertrophy and failure (Vokota, N. et al Am J Hypertens 1995;8:301–310). Further, it is now known that measurement of the circulating levels of different fragments of these hormones in plasma is a powerful means to identify elderly subjects at risk of heart failure (Davis KM. et al. JAAM 1992;267:2625–2629), establish long term prognosis after (myocardial infarction) MI (Hall C. et al J Am Coll Cardiol 1995;26(6):1452–1456), stratify patients in terms of response to angiotensin-converting enzyme inhibition post MI (Motwani JG. et al Lancet 1993;341:1109–1113) and to demonstrate asymptomatic left ventricular dysfunction (Lerman A, Jr. et al Lancet 1993;341:1105–1109; Arad M et al Cardiology 1996;87:12–17).

Myocarditis is also characterized by an increase in synthesis and release of NP from the heart (Takemura G. et al. Int J Cardiol 1995;52:213–22:). While the biological basis of increased production of NP during cardiac hypertrophy and failure is conceptually placed within the re-expression of the cardiac fetal phenotype seen with chronic hemodynamic overload and heart failure, the basis for increased production of NP in myocarditis is not understood. Increased ventricular gene expression in intact cardiocytes surrounding foci of degenerative changes or necrosis has been observed in both animals models and human myocarditis. Mice inoculated with encephalomyocarditis virus, a model of myocarditis with heart failure, showed significantly increased ANF plasma levels and ventricular ANF mRNA 10 and 30 days after infection when compared to non-infected controls (Kanda T. et al. J Pharmacol & Exptl Ther 1995;274:494–498). Treatment of the mice 24 h after inoculation with a combination of the immunomodulators OK432 and human interferon-α A/D prevented the development of cardiomyopathy and hypertrophy and down regulated the expression of ANF mRNA in the ventricles to near normal levels.

W097/32900 (Mischak RP. et al, published Sep. 12, 1997; which is incorporated by reference) discloses monospecific antibodies to hBNP and their use as diagnostic reagents for the detection of BNP levels in plasma of patients with congestive heart disease. The specific epitopes of the MAb's include fragments of the mature BNP ($BNP_{77-108}$) peptide. These fragments include: 5–13 hBNP, 1–10 hBNP, 15–25 hBNP, and 27–32 hBNP.

EP542255 (Tsuji T. et al. published May 19, 1993; which is incorporated by reference) discloses monoclonal antibodies that recognize the C-terminus of hBNP, and the use of these MAb's within RIA's. The assay involves the determination of hBNP in plasma and can be used for the diagnosis of diseases such as hypertension and altered states of the heart and kidney.

Ationu et al (1993a, Cardiovas Res. 27:2135–2139) disclose the monitoring of circulating BNP and ANF levels in paediatric cardiac transplant recipients. In this study increased plasma BNP and ANF levels were noted within patients during the first year after transplant. When BNP levels were re-assayed at 2.5 or 3 years following transplantation, the levels were reduced. Another study (Geny B. et al 1988, J Thorac Cardiovas Surgery 115:473–475) considered the relationship between BNP levels before and immediately following heart transplantation, or coronary artery bypass grafting, and concluded that no meaningful relationship was present. Rather it was observed that following transplantation, plasma BNP levels, which are typically elevated, decreased and returned to earlier levels. Ationu et al (1993b, Cardiovas Res. 27:188–191) disclose the assessment of plasma BNP levels following heart transplantation. Levels of BNP were noted to increase following transplantation, however, there no relationship was observed within plasma or ventricular BNP levels, and rejection episodes. These authors report the desire to derive a non-invasive marker in order to monitor such situations, however, no such relationship was noted with either of these NP's. A similar lack of correlation has been noted in several studies examining circulating ANF levels following cardiac transplantation (e.g. Masters RG. et al Can J. Cardiol 1993,9:609–617).

In all of these studies, there is no disclosure of a relationship between circulating BNP levels and transplant rejection, nor is there any demonstration that circulating BNP levels can be used to monitor cardiac allograph rejection. Rather, several of these references demonstrate the lack of such a correlation, and lack of utility of BNP levels as an indicator of rejection. Even though the prior art has failed to report any meaningful relationship between levels of BNP in biological fluids and transplant rejection, the present invention demonstrates such a relationship, and provides a method for the detection of myocardial allograph rejection by determining BNP levels within biological fluids.

SUMMARY OF THE INVENTION

The present invention relates to a method for the prediction and diagnosis of cardiac allograft rejection involving the determination of brain natriuretic peptide.

According to the present invention there is provided a method of diagnosing cardiac transplant rejection within a patient comprising, obtaining a sample of a biological fluid from said patient, and determining the level of a brain natriuretic peptide (BNP) or a fragment thereof, within said sample of body fluid. This invention also relates to the method as described above wherein said step of determining the concentration of BNP involves an assay comprising at least one antibody exhibiting affinity for said BNP or a fragment thereof. Furthermore, this invention is directed to the method as described above wherein said at least one antibody comprises a polyclonal antibody, a monoclonal antibody, or a combination thereof. This invention is also directed to the above method wherein said biological fluid comprises plasma, urine or cerebrospinal fluid. The present invention also embraces the above method, wherein the BNP is $BNP_{77-108}$, and wherein a level of about or greater than 300 pg/mL of said BNP77–108 within said biological fluid is an indication of a rejection episode.

This invention also relates to a method as defined above, wherein at least two said samples of body fluid from said patient are obtained over a period of time, and the levels within these two samples are compared to determine a change in said BNP levels within said biological fluid.

Furthermore, this invention is directed to the method as defined above, wherein an increase in said level of BNP or fragment thereof is a predictor of transplant rejection. This invention also embraces the method as described above, wherein said BNP is selected from the group consisting of mature BNP or a fragment thereof, and ProBNP or a fragment thereof, or a combination of mature BNP and ProBNP, and wherein said ProBNP comprises $BNP_{1-76}$, $BNP_{1-25}$, or $BNP_{52-76}$, and said mature BNP comprises $BNP_{77-108}$, or a combination of two or more of $BNP_{1-76}$, $BNP_{1-25}$ or $BNP_{52-76}$, and $BNP_{77-108}$.

This invention also embraces the method as described above wherein said assay comprising at least one antibody exhibiting affinity for said BNP or a fragment thereof is selected from the group consisting of RIA, ELISA, fluoroimmunoassay, immunofluorometric assay, and immunoradiometric assay, and wherein the assay is performed in the liquid, or solid phase.

The present invention provides for a method for diagnosing cardiac transplant rejection within a patient by assaying the levels of BNP within biological fluids. Existing methods for determining cardiac transplant rejection require the determination of a range of clinically significant criteria including those based upon tissue biopsy. Even though prior art studies demonstrate a relationship between BNP levels and heart failure, the prior art failed to note any correlation between BNP levels and cardiac rejection. As a result of characterizing the correlation between BNP levels and cardiac rejection, the method of the present invention provides for a sensitive, simple, reliable and effective method for predicting rejection episodes.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
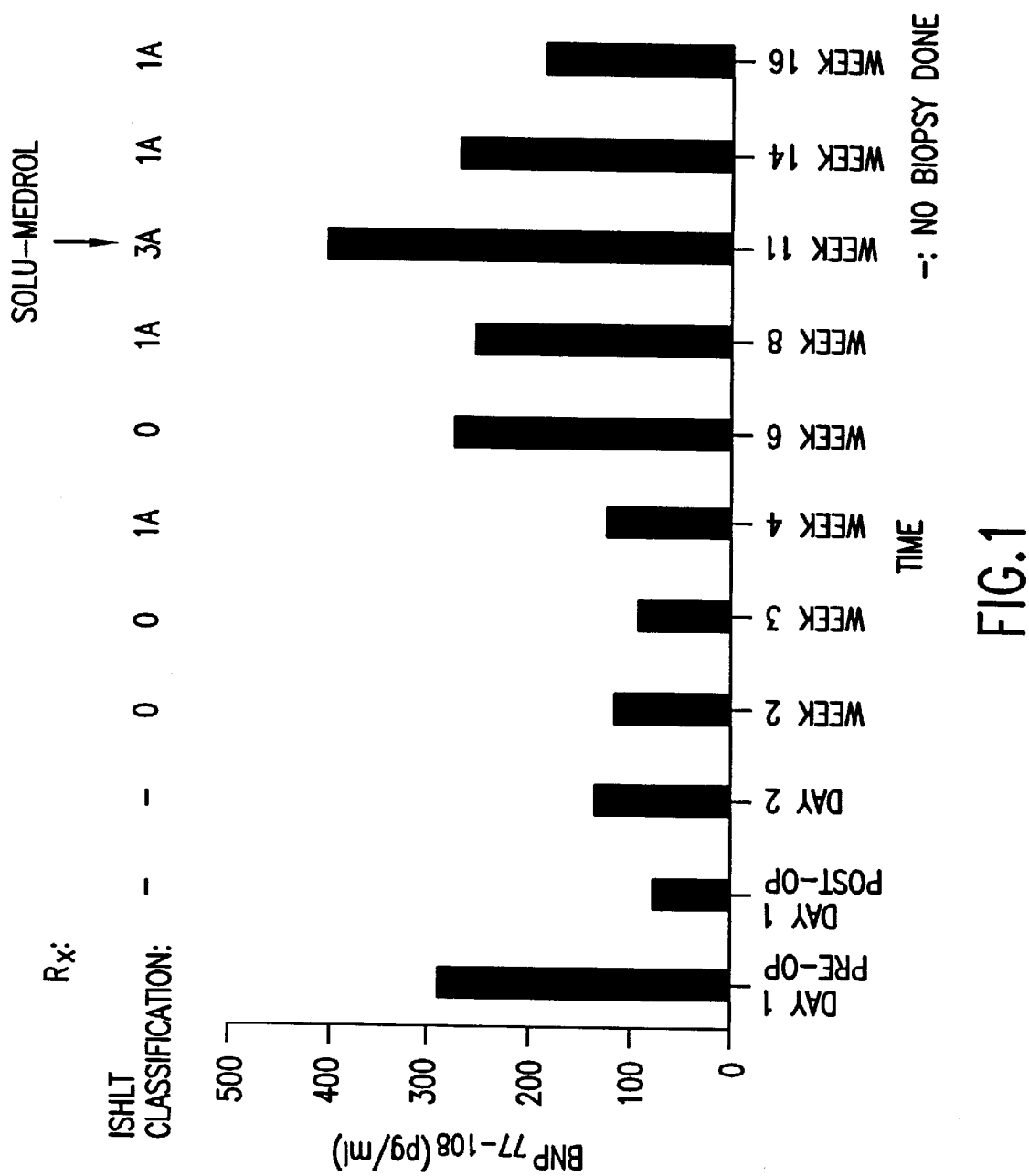
FIG. 1 shows the relationship between plasma $BNP_{77-108}$ levels before and up to 16 weeks following a transplant, and the ISHLT classification. A rejection episode occurred at week 11 (ISHLT classification 3A). Therapeutic treatment for acute rejection was administered during week 11

The present invention relates to a method for the prediction and diagnosis of cardiac allograft rejection involving the determination of natriuretic peptides.

As used herein, ProBNP refers to the entire 1–108 amino acid sequence of the brain natriuretic peptide, and it is also referred to as $BNP_{1-108}$. Specific fragments of BNP are referred to based on the numbering of the ProBNP molecule. For example, the mature, 32 amino acid, active BNP portion is referred to as $BNP_{77-108}$, other fragments used within this invention include the N-terminal portion of ProBNP, for example, which is not to be considered limiting in any manner, $BNP_{1-25}$, and the C-terminal region of the cleaved portion of BNP, for example but not limited to, BNP52–76 (note: $BNP_{52-76}$ is derived from the N-terminal region of ProBNP). However, other portions of the ProBNP molecule may also be suitable for the method of this invention.

A similar nomenclature is used with regards to ANF. The entire ProANF is $ANF_{1-126}$, while specific portions of this peptide are numbered with reference to the ProANF molecule. These fragments include, but are not limited to, $ANF_{1-30}$, $ANF_{74-98}$, $ANF_{99-126}$.

Both the BNP and ANF peptides, or fragments thereof, are detectable within biological fluids, for example plasma, urine and cerebrospinal fluid. The occurrence of these peptides or associated fragments can readily be determined within these biological fluids following the method of this invention as well as using methods known to one of skill in the art.

The term "heart failure", refers to a clinical syndrome in which impaired cardiac pumping decreases ejection and impedes venous return. This is a hemodynamic determination of heart performance. Typically, a heart that exhibits an ejection fraction of less than about 45% (compared to the blood received), is considered to be in heart failure.

By "rejection" or "rejection episode" it is meant a clinically significant determination, based upon a biopsy, that results in an ISHLT (International Society of Heart and Lung Transplantation) Standardized Grading System; Billingham Me. et al J Heart Transplant 1990, 9:587–593) grade of 1 or higher. Such a grade, together with clinical criteria, evident to one of skill in the art, indicates the requirement for boosting the patients immune suppression following a transplantation.

An aspect of the present invention as disclosed herein relates to the determination of plasma BNP levels in diagnosing and predicting rejection in cardiac transplant patients. In addition, the data obtained on NP and gene expression and its relationships to clinical, histopathological and hemodynamic variables help elucidate the pathophysiological basis of rejection and the clinical and molecular determinants of increased NP plasma levels observed after cardiac transplantation and, in general, in cardiac inflammatory disease.

In order to assess the impact of transplantation on BNP circulating levels plasma BNP levels were determined in adult patients undergoing cardiac transplantation. Other studies also assessed the relationship between different portions of BNP in plasma in patients following either transplantation or those exhibiting symptoms of heart failure. ANF plasma levels were also determined in order to establish any relationship between the levels of these peptides in response to rejection episodes or heart failure.

In the context of this invention, methods for the detection of BNP or ANF may include a variety of known techniques that would be evident to one of skill within the art. Such methods include but are not limited to radioimmunoassay (RIA), ELISA, and other immunological-based assays, including fluoroimmunoassay, immunofluorometric assay, and immunoradiometric assay, involving radioactive tracers, colourometric, fluorogenic or enzymatic markers, or chemical luminescence, or immunoturbimetry (e.g. WO97/32900; Mischak RP. et al, published Sep. 12, 1997; which is incorporated by reference; EP542255; Tsuji T. et al. published May 19, 1993; which is incorporated by reference). These immunological assays may involve the use of either polyclonal or monoclonal antibodies, or a combination thereof, that recognize specified portions of either BNP or ANF.

Based upon the results presented below, there is no specific portion of the BNP that is preferred in order to generate these polyclonal or monoclonal antibodies for the purposes of this invention. Rather, any fragment of ProBNP (i.e. $BNP_{1-108}$) or ProANF ($ANF_{1-126}$), may be used for the preparation of antibodies and be suitable for detecting NP levels in order to determine pending rejection episodes. Several of these peptides are also available commercially (e.g. Advanced ChemTech). The antibodies so prepared may be used for the detection of ANF or fragments thereof, or BNP or fragments thereof, or a combination of both ANF and BNP, or a combination of the fragments of ANF or BNP, using the methods as described herein.

Initially, two groups of patients were studied. For those undergoing transplantation during the study period, right heart catheterization and hormonal assays in blood were performed simultaneously immediately pre-operatively and post-operatively at 24 hours and during each endomyocardial biopsy. For those whose transplantation occurred prior to the study period right heart catheterization and hormonal assays in blood were performed during each endomyocardial biopsy. Grading of the degree of cellular rejection was done using the working formulation of the ISHLT.

FIG. 1 shows individual data from a transplant performed during the study period and therefore, pre-transplant plasma $BNP_{77-108}$ are shown. Transplantation resulted in a decrease of plasma $BNP_{77-108}$ levels immediately after transplantation suggesting that the source of this peptide in the pre-transplant period was the diseased ventricle. Plasma $ANF_{99-126}$ levels although decreasing after transplantation, continued to be elevated (data not shown) suggesting that the major contributors of $ANF_{99-126}$ to pre-transplant and post-transplant plasma levels were the atria. Steadily increasing $ANF_{99-126}$ and $BNP_{77-108}$ plasma level preceded an overt rejection episode as assessed by clinical and histological criteria. Further, successful treatment of the rejection episode caused plasma level of both peptides to decrease, although the most noticeable trend was for BNP. It is of interest to note that increased BNP levels are observed several weeks prior (e.g. weeks 6 and 8) to the rejection episode (week 11), yet biopsy analysis produced an ISHLT classification of 0 or 1A.

Figure 2:
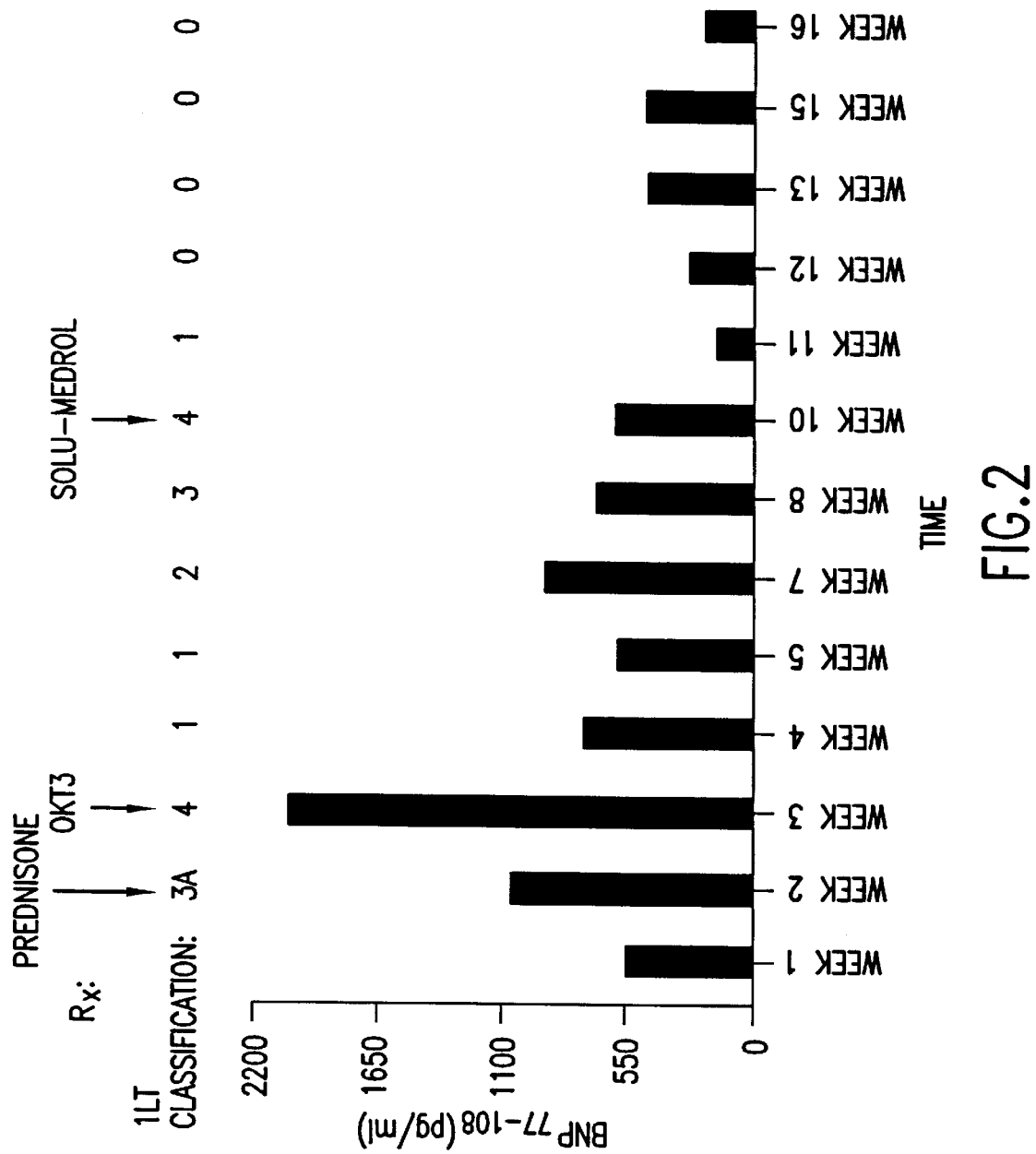
FIG. 2 shows the relationship between plasma $BNP_{77-108}$ levels for 16 weeks following a transplant. An acute rejection episode occurred at weeks 2 ISHLT classification 3A), 3 (ISHLT 4) and 10 (ISHLT 4). Therapeutic treatment was administered during weeks 2, 3 and 10.

FIG. 2 shows a patient who was transplanted prior to the study period and, therefore, pre-transplant $ANF_{99-126}$ and $BNP_{77-108}$ plasma levels could not be determined.

This patient suffered from more serious rejection episodes and, in this and in other cases, the BNP plasma level is correspondingly higher than in patients with milder rejection (Compare y-axis scales between figures).

The temporal pattern of change in plasma levels of $BNP_{77-108}$ in terms of association with rejection episodes was similar to that shown in FIG. 1. However, plasma levels of $ANF_{99-176}$ (data not shown) and $BNP_{77-108}$ (in FIG. 2) were independent of each other during rejection episodes that required additional immunosuppressive treatment.

Some patients were characterized by maintaining consistently higher levels of $ANF_{99-126}$ throughout the study period while others maintained higher $BNP_{77-108}$ plasma levels. Any patient requiring therapeutic intervention due to a rejection episode, however, invariably had relatively higher $BNP_{77-108}$ plasma levels. Furthermore, rejection episodes were preceded by increasing $BNP_{77-108}$ plasma levels.

The relative proportion of mean plasma levels of $ANF_{99-126}$ to $BN_{77-108}$ in individual patients showed widely varying values. A patient with prevalence of $BNP_{77-108}$ had mean plasma levels of $ANF_{99-126}$ of 295.0±19.17 pg/mL and $BNP_{77-108}$ of 677.31±133.69 pg/mL (n=7) while a patient with prevalence of $ANF_{99-126}$ had mean plasma levels of $ANF_{99-126}$ of 192.0±28.9 pg/mL and $BNP_{77-108}$ of 109±17.38 pg/mL (n=13). Overall, plasma $ANF_{99-126}$ levels were slightly lower than those for $BNP_{77-108}$ (239.07±11.54 pg/mL (n=84) and 278.66±34.6 pg/mL (n=84), respectively, p>0.05).

Without wishing to be bound by theory in any manner, it is possible that the ANF plasma levels may be a measure of extracellular volume status while that of BNP indicates cardiac hypertrophy. These underlying events, superimposed to the specific effect(s) of the inflammatory process together with varying degrees of preservation of renal function in individual patients, may explain the variation in NP ratios found.

Only three of the patients included in this pilot study had pulmonary wedge pressure (PWP) and right atrial pressure (RAP) consistently determined at the time of blood sampling for NP determination. Simple correlation analysis of the untransformed data and Bonferroni probability showed that a significant correlation existed between PWP and RAP in the three patients but not between these and ANF or BNP plasma levels or between NP levels themselves. Lack of correlation between cardiac filling pressures and ANF plasma levels has been previously reported for transplant patients (Hare J.M et al Am J Cardiol 1991, 67:391–397) although others (Magoverne J. A. et al, J Heart Trasnpl. 1987, 6:193–198) report a good correlation between these parameters. It is likely that the differences in volume status and cardiac factors and degrees of rejection as outlined above may also explain these differences. Indeed, simple inspection of the correlation curves reveals that outliers leading to declare non-significant correlations between NP or between NP and cardiac filling pressures are often those NP values that are associated with clinically significant rejection episodes requiring aggressive treatment. These findings clearly suggest that in those cases rejection, and not filling pressures, is a major determinant of NP, particularly $BNP_{77-108}$, plasma levels.

These data indicate that rejection episodes needing therapeutic intervention are associated with $BNP_{77-108}$ plasma levels greater than 300–400 pg/mL. The values shown in FIGS. 1 and 2 also suggest that pooling of cardiac hormone levels data in the general population of cardiac transplant patients could lead to declare non-significant associations between increasing plasma $BNP_{77-108}$ and clinically significant rejection episodes because each patient evolves from its own baseline.

In no instance were $BNP_{77-108}$ plasma levels of over 300 pg/mL observed without association with a rejection episode. This observation indicates that the determination of plasma $BNP_{77-108}$ has few false positives. Conversely, all rejection episodes that required additional immunosuppressive therapy were always associated with, and preceded by, an increase of $BNP_{77-108}$ plasma levels. In an instance of difficult histopathological diagnosis, a tentative grading of ISHLT=3A (multifocal moderate rejection) that would be expected to be associated with additional immunosuppressive therapy, BNP levels were in a downward trend and at 40 pg/mL on the day of the biopsy. These levels were well below an average of 1,150 pg/mL (range 300–2480 pg/mL) seen in association with additional immunosuppressive therapy and clinical indications of rejection in other patients. On clinical basis, no additional treatment was given to this patient despite a possible 3A grade and none was required 3 weeks later when a biopsy was graded "0" and BNP levels were 25 pg/mL. This incident further emphasizes the occasional problem encountered with biopsy sampling and the value of investigating BNP as a marker of rejection.

Finally, in all instances studied, mild rejection (lymphocytic infiltrate without cardiocyte necrosis) leading to a more serious rejection episode was accompanied by an increase in plasma BNP levels. The studies as described herein therefore indicate that BNP plasma levels are useful in predicting the outcome of rejection episode, and can be used as an means for determining the need for administering immunosuppressive therapy.

Even the simplest of the methods developed to date for the measurement of ANF or BNP require facilities that are only found in tertiary care facilities. Even then, collection of blood samples is often subjected to variations that are not acceptable in the quantitation of hormones that circulate at concentrations of pg per mL. In addition, most procedures require the handling of radioactive materials and take long processing time when compared to biopsies. For these reasons, the feasibility of replacing the measurement of $BNP_{77-108}$ with assays to quantitate NP fragments that are known to circulate at much higher concentrations is important. Higher concentration of peptide could be detected with faster, simpler and inexpensive technology. In order to enhance the sensitivity for the detection of circulating levels of BNP, a comparison between different portions of ProBNP and $BNP_{77-108}$ were examined.

Plasma N-terminal portion of BNP was compared to $BNP_{77-108}$ by radioimmunoassay the following values were obtained: N-terminal portion=$2,895 \pm 513$ pg/mL (n=31) and for $BNP_{77-108}$=$279 \pm 34$ (n=84). Pairwise comparison of samples for which both values were available in the same sample (n=19) gave a correlation coefficient (Pearson's)= 0.969 (Bonferroni p<0.0001). Furthermore, the average levels of $BNP_{1-25}$ are up to 10 fold higher than the levels of $BNP_{77-108}$ (see Tables 1 and 2 "Means") . An assessment of plasma $BNP_{77-108}$, $BNP_{1-25}$, and $BNP_{52-76}$ levels in patients following transplantation (FIG. 3) and heart failure (FIG. 4) indicated that the circulating levels of the N-terminal, and C-terminal region of the cleaved portion of ProBNP are highly correlated with levels of $BNP_{77-108}$. The detection of $BNP_{1-25}$ and $BNP_{52-76}$ also includes detection of $BNP_{1-108}$ and possible other BNP species within the plasma.

As a result of the high degree of correlation between the cleaved N-terminal and C-terminal portions of the cleaved portion of the peptide and the mature peptide in plasma obtained from transplant and heart failure patients, and as a result of the high levels of these peptides within plasma, the detection of any portion of the BNP peptide may be used as an indicator of rejection episodes, heart failure or other heart disease. These results indicate that plasma BNP levels may be determined with techniques that are less sensitive, less exacting, less expensive and faster as would be achieved by replacing the radioimmunoassay by a calorimetric technique. Such technique would also be of general applicability for other diagnostic and prognostic purposes in cardiology.

While this invention is described in detail with particular reference to preferred embodiments thereof, said embodiments are offered to illustrate but not limit the invention.

EXAMPLES

Patients undergoing orthotopic cardiac transplantation at the University of Ottawa Heart Institute were studied. Parallel, hemodynamic, neuroendocrine and histopathological measurements were made.

It is the standard of care that patients undergoing transplantation immediately prior to surgery have the right internal vein cannulated for measurement of intra-cardiac pressures including the right atrial, pulmonary arterial and pulmonary capillary wedge pressures. Blood samples are withdrawn from the right atrium for assays of ANF and BNP. On day 1 following transplantation prior to removal of the cannula from the jugular vein the pressures are measured and blood taken for the hormonal assays. Subsequently it is routine for these patients to undergo right heart catheterization and endomyocardial biopsy at a decreasing frequency and as guided by the clinical circumstances. This is performed on an out-patient basis. During this procedure the internal jugular vein is cannulated, the intra-cardiac pressures are measured and a sample of tissue from the right ventricular endomyocardium is removed for histopathological assessment. At this time blood is collected again for hormonal assays. Patients are followed for a period of time following their transplant during which time each patient will have catheterizations and biopsies. Hormonal assays are performed during each such procedure.

Typically, a histological grading of the biopsy of ISHLT grade 3A or higher is considered clinically significant rejection necessitating a boost in the patient's immune suppression. Typical maintenance immune suppression for patients consists of oral cyclosporine, azathioprine and prednisone. In the case of rejection this is supplemented by three days of pulse high dose intravenous steroids. Recalcitrant rejection requires the use of such drugs as OKT3 (monoclonal antibody against T3 lymphocytes).

Biopsy And Blood Processing

Four to six biopsies obtained from routine percutaneous transvenous right ventricular endomyocardial biopsies are fixed in 10% neutral buffered formalin, paraffin embedded and sectioned as to obtain five micron step sections through the entire block. An average four to seven glass slides with three to four sections at each level are stained with Haematoxylon-phloxine-saffron and interpreted by a cardiovascular pathologist. Grading of the degree of cellular rejection is done using the working formulation of the International Society for Heart and Lung Transplantation Standardized Grading System (Billigham Me. et al J Heart Transpl. 1990, 9:587–593).

Two 15 mL blood samples are collected per patient prior to and within 24 of cardiac transplantation and each time right heart catheterization is performed, in pre-chilled Vacutainer™ tubes with EDTA anticoagulant. The blood is centrifuged immediately at 4° C. and the plasma kept at −80° C. until one tube is extracted for determination of $ANF_{99-126}$ and $BNP_{77-108}$. The plasma of the second tube is used for analysis using assays for proBNP fragments ($BNP_{1-25}$ and $BNP_{52-76}$)

Extraction Of Plasma And Tissue For Radioimmunoassay

Plasma samples are acidified by adding 100 μl/mL of I M HCI and passed through Sep-Pak $C_{18}$ cartridges (Millipore, Milford, Mass.) pre-wetted with 5 mL of 80% acetonitrile (ACN) in 0.1% trifluoroacetic acid (TFA) and 10 mL of 0.1% TFA. The cartridges with the absorbed peptides will be washed with 20 mnL of 0.1% TFA, and then eluted with 3 mL of 60% ACN in 0.1% TFA. The elates are freeze-dried and processed for radio immunoassay as previously described (Sarda IR. et al. Clin Biochem. 1989 22:11–15).

Assayfor N-terminal (NT—) BNP

For the purposes of developing a simpler method to measure NT-BNP, an ELISA protocol is pursued. Two approaches are possible for measuring soluble antigens with ELISAs: 1. Technology based on a direct competitive protocol, or, 2. Technology based on a "sandwich" technique involving a competitive reaction plus a reaction with a second antibody directed to a second epitope in the antigen. A capture and secondary polyclonal and monoclonal antibodies against the N-terminal portion of $BNP_{52-76}$ used is:
Lys—Ser—Arg—Glu—Val—Ala—Thr—Glu—Gly—le—Arg—Gly—His—His—Arg—Lys—Met—Val—Leu—Tyr—Thr—Leu—Arg—Ala—Pro—Arg (SEQ ID NO:1)

Production Of Monoclonal Antibodies

Synthetic $NP_{52-76}$ are coupled to bovine thyroglobulin using the carbodiimide method (Skowsky WR et al. 1972, J Lab Clin Med 80:134–144). Female BALBoC mice are immunized with the $BNP_{52-76}$—thyroglobulin conjugates mixed with 100 μg of murarnyl peptide, dissolved in phosphate buffered saline. Protocols for immunization and for the fusion of spleen cells from the immunized mice with cells of the non-secreting mouse SP2-O plasmacytoma line are described in detail, elsewhere (Milne RW. et al 1992, in Immunological Methods for Studying and Quantifying Lipoproteins and Apolipoproteins, Converse CA and Skinner ER eds, Oxford U Press, pp 61–84). Two methods of screening are used to identify specific antibodies in the culture supernatants of hybridomas. In the first protocol, $BNP_{52-76}$ is adsorbed to polystyrene Removal Wells (Dynatech) and after washing and saturation of the wells, they are successively exposed to hybridoma culture supernatant and $^{125}$I-anti-mouse IgG. In the second protocol, wells are coated with affinity-purified, anti-mouse IgG and then successively exposed to hybridoma culture supernatant and to $^{125}$I-$BNP_{52-76}$, as appropriate. Details of the two screening protocols have been reported along with a discussion of their relative merits (Milne RW. et al 1992, in Immunological Methods for Studying and Quantifying Lipoproteins and Apolipoproteins, Converse CA and Skinner ER eds, Oxford U Press, pp 61–84).

Production of Polyclonal Antibodies

Polyclonal antibodies to ANF and BNP are commercially available (e.g. Advanced ChemTech). However, antibodies to specific portion of the BNP molecule are prepared as follows (Sarda IR. et al. Clin Biochem. 1989 22:11–15): 3 mg of peptide in 0.3 mL of 20 mM HCI is mixed with 3 mg of keyhole limpet haemocyanin (Sigma) dissolved in 0.3 mL of 20 mM HCL. Thirty mg of 1-ethyl 3—(3-dimethylaminopropyl) carbodiimide in 0.2 mL of water is added and the reaction allowed to proceed at room temperature for 1 h. After 1 h, 0.6 mL of 20 mM NaOH is added to bring the pH to about 6.5 and left to stand for about 1 h at room temperature and then diluted to 5 mL with 0.9% NaCl. The peptide conjugate is emulsified in twice its volume with complete Freund's adjuvant (Difco Laboratories, Detroit, Michigan). Five 3-month-old New Zealand white rabbits are immunized by injecting the emulsion intramuscularly into the biceps femoralis, so that each animal receives a total of 3 mL of the emulsion. Animals are boosted with the conjugate emulsified with Freund's incomplete adjuvant at 4-week intervals and bled 10–14 days after each booster injection by ear vein puncture. Serum is aliquoted and stored at −70° C. Titres are determined by standard binding curves using a previously published protocol (Sarda IR. et al. Clin Biochem. 1989 22:11–15).

Tracer peptides are iodinated using the chloramine T method or the Bolton-Hunter reagent as appropriate and previously published (Sarda IR. et al. Clin Biochem. 1989 22:11–15). Purification is carried out by RP-HPLC using a Vydac $C_{18}$ column and a 60-min gradient of 8–35% acetonitrile containing 0.1% TFA at a flow rate of 1.5 mL/ min. The specific activity of labelled peptides is determined using the self-displacement method described by Morris (1976, Clin Chem Acta 73:213–216).

Alkaline phosphatase-antibody conjugates for ELISAs are prepared from affinity purified polyclonal or monoclonal antibodies and alkaline phosphatase (enzyme immunoassay grade, Boehringer-Mannheim) according to standard methodology (van Vunakis H, Langone JJ. 1980 Immunological Techniques, pp. 1–525)

Statistical Analysis

Correlation analysis with posthoc test for statistical significance are carried out between continuous variables using standard procedures. Multivariate analysis (SYSTAT, an SPSS statistical package) is used to examine the independent predictive value of BNP values and rejection versus other risk factors including age, disease, sex, etc . . . Receiver-operating analysis (reference) is carried out to determine the relationship between sensitivity and specificity of BNP plasma values at different diagnostic cutoff values. The data of FIG. 3 and 4 were generated using the SYSTAT Graph Module.

Results

Data obtained from a transplant performed during the study period including pre-transplant plasma $ANF_{99-126}$ and $BNP_{77-108}$ are shown in FIG. 1. The study period covered a 16 week period. Following transplantation, a decrease of plasma $BNP_{77-108}$ levels is observed. Plasma $ANF_{99-126}$ levels also decreased after transplantation, but continued to be elevated throughout the monitoring period. Plasma levels of both $ANF_{99-126}$ and $BNP_{77-108}$ increased with the onset of a rejection episode (ISHLT 3A). Following treatment of the rejection episode plasma levels of both peptides decreased, most noticeably for $BNP_{77-108}$.

Results from a patient, transplanted prior to the study period are shown in FIG. 2. Two serious rejection episodes were noted during this study (weeks 2,3 and 10), and both corresponded with increased levels of plasma $BNP_{77-108}$ (see weeks 2, 3 and 7). A corresponding increase in the levels of ANF were not detected This and other analysis have also indicated that the $BNP_{77-108}$ plasma level is higher in patients with more sever rejection episodes. Furthermore, if therapeutic intervention due to a rejection episode was required, plasma levels of $BNP_{77-108}$ were also noted to be comparatively higher. In all cases however, rejection episodes were preceded by increasing $BNP_{77-108}$ plasma levels.

The relative proportion of mean plasma levels of $ANF_{99-126}$ to $BNP_{77-108}$ in individual patients showed widely varying values. A patient with prevalence of $BNP_{77-108}$ had mean plasma levels of $ANF_{99-126}$ of $295.0\pm19.17$ pg/mL and $BNP_{77-108}$ of $677.31\pm133.69$ pg/niL (n=7) while a patient with prevalence of $ANF_{99-126}$ had mean plasma levels of $ANF_{99-126}$ of $192.0\pm28.9$ pg/mL and $BNP_{77-108}$ of $109\pm17.38$ pg/mL (n=13). Overall, plasma $ANF_{99-126}$ levels were slightly lower than those for $BNP_{77-108}$ ($239.07\pm11.54$ pg/mL (n=84) and $278.66\pm34.6$ pg/mL (n=84), respectively, p>0.05).

Figure 3:
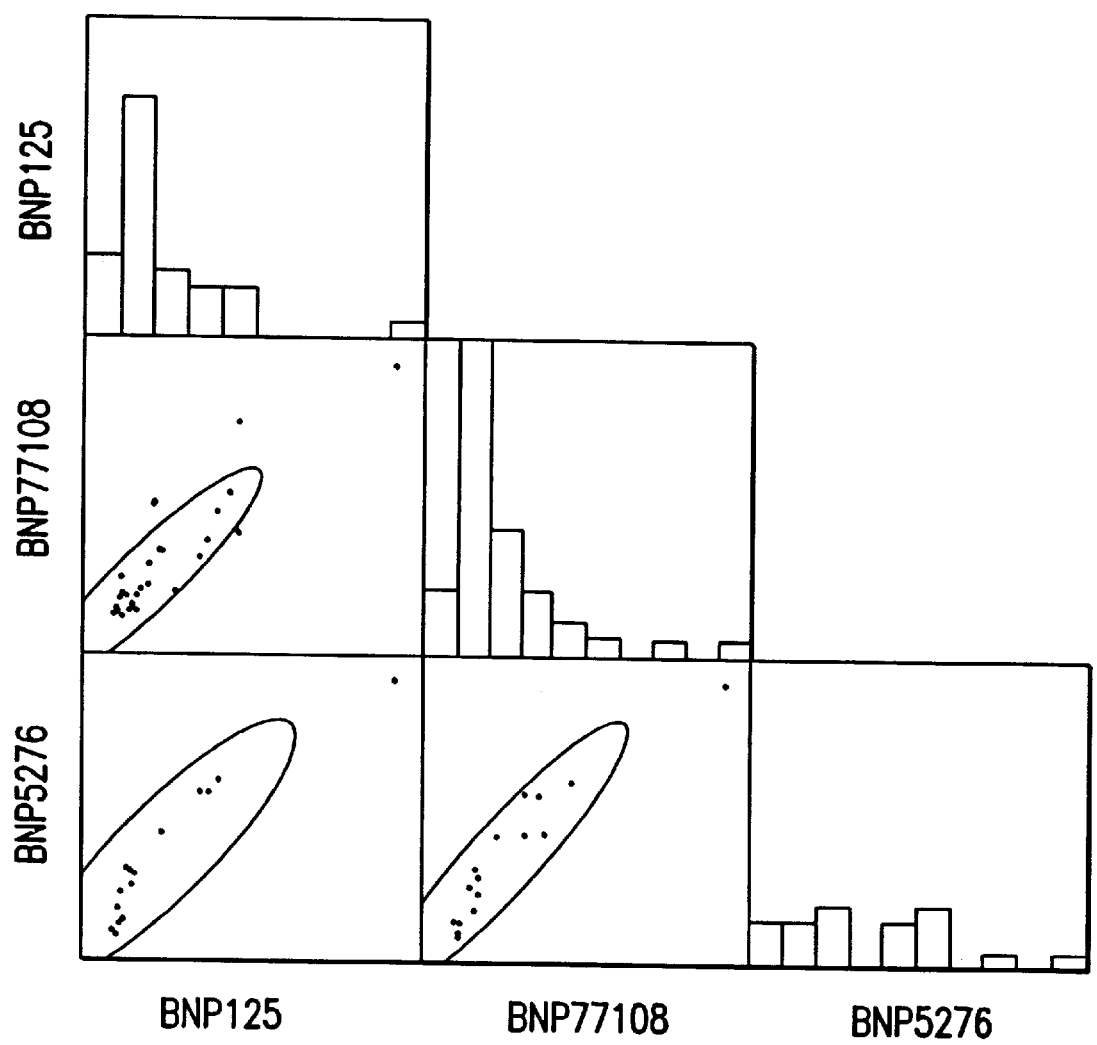
FIG. 3 shows the correlation between plasma $BNP_{1-25}$, $BNP_{77-108}$ and $BNP_{2-76}$ levels in transplant patients. Also shown is the frequency histogram for each variable.

An assessment of the use of other portions of the BNP molecule for determining the onset of transplant rejection in 19 patients is shown in FIG. 3. The correlation in plasma levels between each of the portion of BNP tested and BNP77–108 is shown in Table 1.

TABLE 1

Pearson Correlation Matrix and Matrix of Bonferroni Probabilities for the data presented in FIG. 3 (n = 19)

| Means: | $BNP_{1-25}$ 3.263 ng $BNP_{1-25}$ | $BNP_{77-108}$ 490.640 pg $BNP_{77-108}$ | $BNP_{52-76}$ 486.016 pg $BNP_{52-76}$ |
|---|---|---|---|
| Pearson Correlation Matrix | | | |
| $BNP_{1-25}$ | 1.000 | — | — |
| $BNP_{77-108}$ | 0.969 | 1.000 | — |
| $BNP_{52-76}$ | 0.866 | 0.920 | 1.000 |

TABLE 1-continued

Pearson Correlation Matrix and Matrix of Bonferroni Probabilities for the data presented in FIG. 3 (n = 19)

| Means: | $BNP_{1-25}$ 3.263 ng $BNP_{1-25}$ | $BNP_{77-108}$ 490.640 pg $BNP_{77-108}$ | $BNP_{52-76}$ 486.016 pg $BNP_{52-76}$ |
|---|---|---|---|
| Matrix of Bonferroni Probabilities | | | |
| $BNP_{1-25}$ | 0.0 | — | — |
| $BNP_{77-108}$ | 0.000 | 0.0 | — |
| $BNP_{52-76}$ | 0.000 | 0.000 | 0.0 |

Bartlett Chi-Square statistic: 76.539 df = 3; Prob = 0.000

These results indicate that fragments, in addition to $BNP_{77-108}$, of the ProBNP molecule may be effectively used for the determination of plasma BNP levels. Due to the higher levels of $BNP_{55-76}$ and $BNP_{1-25}$ present within plasma, assays based on these fragments provide a more sensitive monitoring of plasma BNP levels.

Figure 4:
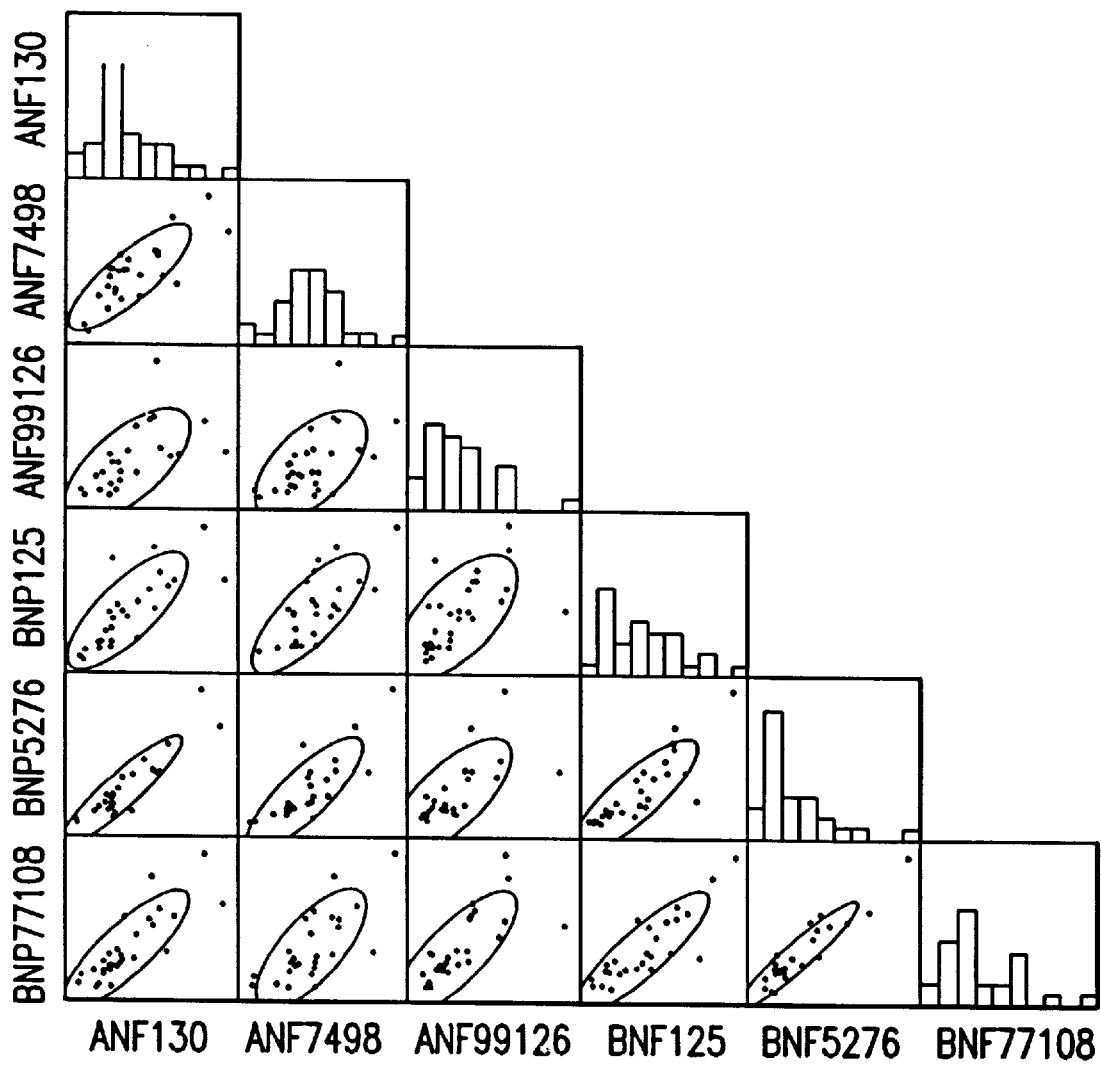
FIG. 4 shows the correlation between plasma $ANF_{1-30}$, $ANF_{74-98}$, $ANF_{99-126}$, BNP1–25, $BNP_{52-76}$, $BNP_{77-108}$ levels in patients diagnosed with heart failure. Histograms

The levels of BNP and ANF were also determined in 27 patients diagnosed as exhibiting heart failure. the results of such a study are shown in FIG. 4 and Table 2.

TABLE 2

Pearson Correlation Matrix and Matrix of Bonferroni Probabilities for the data presented in FIG. 4 (n = 27)

| Means: | $ANF_{1-30}$ 6.536 ng $ANF_{1-30}$ | $ANF_{74-98}$ 2.903 ng $ANF_{74-98}$ | $ANF_{99-126}$ 119.84 pg $ANF_{99-126}$ | $BNP_{1-25}$ 1.369 ng $BNP_{1-25}$ | $BNP_{77-108}$ 154.239 pg $BNP_{77-108}$ | $BNP_{52-76}$ 503.749 pg $BNP_{52-76}$ |
|---|---|---|---|---|---|---|
| Pearson Correlation Matrix | | | | | | |
| ANF1–30 | 1.000 | — | — | — | — | — |
| ANF74–98 | 0.806 | 1.000 | — | — | — | — |
| ANF99–126 | 0.627 | 0.559 | 1.000 | — | — | — |
| $BNP_{1-25}$ | 0.773 | 0.776 | 0.525 | 1.000 | — | — |
| $BNP_{77-108}$ | 0.925 | 0.815 | 0.655 | 0.825 | 1.000 | — |
| $BNP_{52-76}$ | 0.856 | 0.741 | 0.716 | 0.833 | 0.936 | 1.000 |
| Matrix of Bonferroni Probabilities | | | | | | |
| $ANF_{1-30}$ | 0.0 | — | — | — | | |
| $ANF_{74-96}$ | 0.000 | 0.0 | — | — | | |
| $ANF_{99-126}$ | 0.007 | 0.036 | 0.0 | — | | |
| $BNP_{1-25}$ | 0.000 | 0.000 | 0.074 | 0.0 | | |
| $BNP_{77-108}$ | 0.000 | 0.000 | 0.003 | 0.000 | 0.0 | — |
| $BNP_{52-76}$ | 0.000 | 0.000 | 0.000 | 0.000 | 0.000 | 0.0 |

Bartlett Chi-Square statistic: 170.933; df = 15; Prob = 0.000

These results again indicate the high degree of correlation between different portions of the BNP or ANF molecules with the biologically active BNP or ANF peptides. Furthermore, these results demonstrate the utility of BNP, or a fragment thereof, for the diagnosis of heart failure and other heart related diseases.

All publications referred to herein are incorporated by reference.

The present invention has been described with regard to preferred embodiments. However, it will be obvious to persons skilled in the art that a number of variations and modifications can be made without departing from the scope of the invention as described herein.

What is claimed is:

1. A method of diagnosing cardiac transplant rejection episode within a patient comprising, obtaining a sample of a biological fluid from said patient, and determining the level of a brain natriuretic peptide (BNP) or a fragment thereof, within said sample of body fluid, wherein an increase in said level of BNP or fragment thereof is an indication of a rejection episode.

2. The method of claim 1 wherein said step of determining the level of BNP involves an assay utilizing at least one antibody exhibiting affinity for said BNP or a fragment thereof.

3. The method of claim 1 wherein said biological fluid comprises plasma.

4. The method of claim 1 wherein said biological fluid comprises urine.

5. The method of claim 1 wherein said biological fluid comprises cerebrospinal fluid.

6. The method of claim 2 wherein said at least one antibody comprises a polyclonal antibody, a monoclonal antibody, or a combination thereof.

7. The method of claim 6 wherein said at least one antibody comprises a polyclonal antibody.

8. The method of claim 6 wherein said at least one antibody comprises a monoclonal antibody.

9. The method of claim 2 wherein the step of obtaining a sample of a biological fluid from said patient, comprises obtaining at least two of said samples of body fluid from said patient over a period of time.

10. The method of claim 9 wherein the step of determining the level of BNP or fragment thereof, comprises determining said level of BNP or fragment thereof within said at least two of said samples of body fluid, and comparing said levels to determine a change in said BNP levels within said biological fluid.

11. The method of claim 2 wherein said BNP is selected from the group consisting of mature BNP or a fragment thereof and ProBNP or a fragment thereof, or a combination of mature BNP or a fragment thereof, and ProBNP or a fragment thereof.

12. The method of claim 11 wherein said ProBNP comprises $BNP_{1-76}$.

13. The method of claim 12 wherein said ProBNP comprises $BNP_{1-25}$.

14. The method of claim 12 wherein said ProBNP comprises $BNP_{52-76}$.

15. The method of claim 11 wherein said mature BNP comprises $BNP_{77-108}$.

16. The method of claim 2 wherein said assay utilizing at least one antibody exhibiting affinity for said BNP or a fragment thereof is selected from the group consisting of RIA, ELISA, fluoroimmunoassay, immunofluorometric assay, and immunoradiometric assay.

17. The method of claim 16 wherein the assay is performed in the liquid, or solid phase.

18. The method of claim 16 wherein the assay is RIA.

19. The method of claim 16 wherein the assay is ELISA.

20. A method of diagnosing cardiac transplant rejection episode within a patient, comprising: obtaining a sample of a biological fluid from said patient; and determining the level of brain natriuretic peptide (BNP) fragment $BNP_{77-108}$ within said sample of body fluid, wherein a level of said $BNP_{77-108}$ of about or greater than 300 pg/ml within said biological fluid is an indication of a rejection episode.

21. The method of claim 20 wherein said step of determining the level of $BNP_{77-108}$ involves an assay utilizing at least one antibody exhibiting affinity for said $BNP_{77-108}$.

22. The method of claim 20 wherein said biological fluid is selected from the group consisting of plasma, urine and cerebrospinal fluid.

23. The method of claim 21 wherein said at least one antibody comprises a polyclonal antibody, a monoclonal antibody, or a combination thereof.

24. The method of claim 21 wherein said assay utilizing at least one antibody exhibiting affinity for said $BNP_{77-108}$ is selected from the group consisting of RIA, ELISA, fluoroimmunoassay, immunofluorometric assay, and immunoradiometric assay.

25. The method of claim 24 wherein the assay is performed in the liquid, or solid phase.

26. The method of claim 24 wherein the assay is RIA.

27. The method of claim 24 wherein the assay is ELISA.

* * * * *

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: N terminal of
      BNP52-76

<400> SEQUENCE: 1

Lys Ser Arg Glu Val Ala Thr Glu Gly Ile Arg Gly His His Arg Lys
 1               5                  10                  15

Met Val Leu Tyr Thr Leu Arg Ala Pro Arg
                20                  25